United States Patent [19]

Behling

[11] 4,270,994
[45] Jun. 2, 1981

[54] ELECTROCHEMICAL DEHYDROGENATION OF STEROIDAL $\Delta^{3,5}$ ENOL ETHERS UNDER BASIC CONDITIONS TO PROVIDE STEROIDAL $\Delta^{4,6}$ DIENONES

[75] Inventor: James R. Behling, Lindenhurst, Ill.

[73] Assignee: G. D. Searle & Co., Chicago, Ill.

[21] Appl. No.: 122,938

[22] Filed: Feb. 20, 1980

[51] Int. Cl.³ .............................................. C25B 3/02
[52] U.S. Cl. ........................................ 204/78; 204/72
[58] Field of Search .................................. 204/72, 78

[56] References Cited

U.S. PATENT DOCUMENTS

| | | | |
|---|---|---|---|
| 3,485,829 | 12/1969 | Fried | 204/78 |
| 3,491,090 | 1/1970 | Fried | 204/78 |
| 3,873,580 | 3/1975 | Rennie | 204/78 |

FOREIGN PATENT DOCUMENTS

| | | | |
|---|---|---|---|
| 7507398 | 6/1974 | Netherlands | 204/72 |

OTHER PUBLICATIONS

Pradham et al., J. Organ. Chem. 29, pp. 601–604, (1964).
Fried et al., Organic Reactions in Steroid Chem., vol. 1, pp. 308,313, (Van Nostrand), 1972.
Walker et al., Chem. Rev., 67, pp. 153–195, (1967).
Burn et al., Chem. and Industry, p. 497, (1966).
Bunker et al., Synthesis, p. 671, (1975).
Jackman, Advances in Organic Chem., vol. 2, pp. 329–333, (Interscience Publishers), 1960.

*Primary Examiner*—R. L. Andrews
*Attorney, Agent, or Firm*—James G. Passe; Mary Jo Kanady; Joyce Niblack

[57] ABSTRACT

An improved process for the preparation of steroidal $\Delta^{4,6}$dienones by the electrochemical dehydrogenation of the corresponding $\Delta^{3,5}$enol ethers under basic conditions, using less than stochiometric amounts of a high potential catalyst, such as 2,3-dichloro-5,6-dicyano-benzoquinone, in a partially aqueous electrolyte solution.

23 Claims, No Drawings

4,270,994

ELECTROCHEMICAL DEHYDROGENATION OF STEROIDAL $\Delta^{3,5}$ ENOL ETHERS UNDER BASIC CONDITIONS TO PROVIDE STEROIDAL $\Delta^{4,6}$ DIENONES

BACKGROUND OF THE INVENTION

In view of the importance of steroids as therapeutic agents, there has been considerable effort spent in developing improved processes for preparing various steroidal species.

One such development has centered on the dehydrogenation of steroidal $\Delta^{3,5}$enol ethers with 2,3-dichloro-5,6-dicyanobenzoquinone and similar reagents. See for example, Pradham et al., "The Dehydrogenation of Steroidal $\Delta^{3,5}$Enol Ethers with Dichlorodicyanobenzoquinone(DDQ)", *J. Organ. Chem.*, 29, pp. 601–604(1964); Fried et al., *Organic Reactions in Steroid Chemistry*, Vol. 1, pp. 308–313(Van Nostrand Reinhold Company, New York, 1972); and Walker et al., "2,3-Dichloro-5,6-Dicyanobenzoquinone and Its Reactions", *Chem. Rev.*, 67, pp. 153–195(1967).

Burn et al., *Chemistry and Industry*, p. 497(1966) reported the formation of 17-α-acetoxy-6-hydroxymethyl-3-methoxypregna-4,6-diene-20-one with 2,3-dichloro-5,6-dicyanobenzoquinone(DDQ) as the reagent in aqueous acetone and suggested extension of that reaction to other 3-alkoxy-6-hydroxymethyl-4,6-dien-3-ones in the androstane, 19-norandrostane, pregnane and corticoid species.

It has now been found that the yields can be improved and other advantages obtained by the electrochemical dehydrogenation of the $\Delta^{3,5}$enol ethers with 2,3-dichloro-5,6-dicyanobenzoquinone, or another suitable high potential quinone, in a basic system. This process provides an unexpected increase in the yields obtained by the chemical dehydrogenations of the prior art, has the further advantage of providing end product of greater purity, is a cleaner reaction, is operable with catalytic or less than stoichiometric amounts of the quinone, and further allows for the regeneration and recovery of the catalyst when 2,3-dichloro-5,6-dicyanobenzoquinone or 2,3-dichloro-5,6-dicyanohydroquinone is employed. In both cases, DDQ is recovered. The results obtained are particularly surprising since the quinones are base sensitive.

The regeneration and recovery of 2,3-dichloro-5,6-dicyanobenzoquinone by the anodic oxidation of 2,3-dichloro-5,6-dicyanohydroquinone has been reported by Brinker et al. *Synthesis*, p. 671(1975). However, there has been no suggestion of using the quinones in electrochemical dehydrogenation of steroids. Other high potential quinones useful in the practice of the present invention are disclosed by Jackman, "Hydrogenation-Dehydrogenation Reactions", *Advances in Organic Chemistry*, Vol. 2, pp. 329–333(Interscience Publishers, Inc., New York, 1960).

SUMMARY

The present invention provides an improved process for the preparation of steroidal $\Delta^{4,6}$dienones by the electrochemical dehydrogenation of the corresponding $\Delta^{3,5}$enol ethers under basic conditions, using less when stochiometric amounts of a high potential catalyst, such as 2,3-dichloro-5,6-dicyanobenzoquinone as a catalyst, in a partially aqueous electrolyte solution.

DETAILED DESCRIPTION OF PREFERRED EMBODIMENTS

The improved process of preparing steroidal $\Delta^{4,6}$dienones of the present invention comprises the electrochemical dehydrogenation of steroidal $\Delta^{3,5}$enol ethers to their corresponding $\Delta^{4,6}$dienones in high yields. The dehydrogenation is accomplished by anodic oxidation using 2,3-dichloro-5,6-dicyanobenzoquinone, 2,3-dichloro-5,6-dicyanohydroquinone or another suitable high potential catalyst, as a catalytic electron carrier. The reaction is carried out under basic conditions in a partially aqueous electrolyte system as described in detail hereinbelow.

The process of the present invention can be carried out either by batch method in a divided or undivided cell, or in a continuous flow system. In the case of divided cells, suitable cell dividers inlcude ion exchange membranes such as DuPont's Nafion ® polyhalogenated teflon membranes or other suitable porous dividers, i.e., sintered glass, ceramics, etc.

For purposes of illustration, the invention is described using a divided H cell having a carbon anode with a silver/silver nitrate reference electrode and a platinum cathode.

Generally speaking, the enol ether, catalyst, solvent and base are placed in the anode compartment of a H cell along with a suitable reference electrode such as a silver/silver nitrate electrode. The electrolyte solution is placed in the cathode chamber along with a suitable cathode such as a 6 cm×2 cm platinum foil sheet. Sufficient cell voltage is applied such that current passes and the reaction proceeds for a period of time sufficient to complete the reaction, generally from about 2 to about 5 hours, and the dienone is recovered and isolated using standard methods.

The addition of a basifying agent, such as a soluble or partially soluble carbonate, bicarbonate, oxide, hydroxide and the like to the anolyte improves the effectiveness of the process as does agitation of the electrolyte solution.

The term "catalyst" refers to high potential quinones. The preferred catalyst is 2,3-dichloro-5,6-dicyanobenzoquinone. Other high potential catalysts can be employed in the practice of this invention. The term "high potential catalysts" includes 2,3-dichloro-5,6-dicyanobenzoquinone, 2,3-dichloro-5,6-dicyanohydroquinone, 3,3',5,5'-tetrachloro-4,4'-diphenoquinone, tetrachloro-1,2-benzoquinone and the like. Chloranil can also be employed under appropriate conditions. Since 2,3-dichloro-5,6-dicyanohydroquinone is converted to 2,3,-dichloro-5,6-dicyanobenzoquinone by anodic oxidation during the reaction, the starting catalyst can be either the benzoquinone, the hydroquinone or a mixture. Since 2,3-dichloro-5,6-dicyanobenzoquinone is regenerated during the reaction, the catalyst can be recovered and reused. While it is necessary to use one mole of 2,3-dichloro-5,6-dicyanobenzoquinone in conventional chemical conversions, catalytic or less than stoichiometric amounts can be employed in the practice of this invention. It is preferred to use from 2.5 to 10 weight percent of catalyst based on the steroid weight.

The electrochemical dehydrogenation is advantageously conducted under basic conditions which adds to the stability of the enol ether under the reaction conditions. Suitable bases employed in the present invention are insoluble or partially soluble bases which do not affect lactone chemistry. Preferred bases include salts of alkali and alkaline earth metals such as sodium bicarbonate, sodium carbonate, lithium carbonate, calcium carbonate, magnesium carbonate and the like. Carbonates and bicarbonates are the preferred salts, although it will be apparent to those skilled in the art that other salts can be employed in this invention. The insoluble or partially soluble bases are employed in amounts of between 25 percent to 50 percent by weight of steriod. For optimum conditions, at least 1 equivalent or 2 moles of base are employed.

Suitable electrolytes for use in the present invention are inert soluble salts which are stable to oxidation, such as the borates, chlorides, perchlorates, sulfonates, phosphates and fluoroborates of lithium and tetraalkylammonium and the like, i.e. tetrabutylammoniumfluoroborate, tetraethylammonium fluoroborate, lithium perchlorate, lithium chloride and the like. The electrolyte salts are employed in amounts of from about 5 percent to about 300 percent by weight of the steroid, preferably from about 10 percent to about 150 weight percent.

The solvent system employed in this invention is a partially aqueous polar organic solvent system, i.e. 10–50 percent aqueous acetonitrile, dimethylformamide, dioxane, nitromethane or other suitable high dielectric solvents.

The preferred anode material is carbon. Other suitable anode materials include, but are not limited to, platinum and other suitable stable metal oxides such as $PbO_2$, $SnO_2$, $TiO_2$ and the like.

The preferred cathode materials are platnimum and stainless steel. However, any other low hydrogen overvoltage material that evolves hydrogen from an aqueous electrolyte can be employed, i.e. rhuthenium, nickel and the like.

It is necessary to conduct the reaction at sufficient applied voltage that current passes, phenol is oxidized and the desired product is obtained. The anode potential varies with the solvent, electrolyte, catalyst, pH and anode material. The potential is determined for a given $\Delta^{3,5}$enol ether substrate by cyclic votammetry. The potential selected is such that the phenol is oxidized but also such that the substrate molecule is inert to the anode in the absence of phenol. Generally, for the compounds used for illustration purposes herein, a potential of up to 1.5 V vs. $Ag/AgNO_3$ is employed. In the case of a $Ag/AgNO_3$ reference electrode, potentials of from +0 to 1.5 V are employed. The preferred potential is +0.7 V.

It will be understood by those skilled in the art that if a reference electrode other than $Ag/AgNO_3$ is employed, for example, standard calomel electrode (SCE), the applied potential would be adjusted accordingly, to, for example, between +0 to +1.2, preferably about +0.4 V.

For optimal results, it is necessary to pulse the anode to a cathodic potential of not more than −0.5 V for 3 seconds every 30 seconds.

It is wholly surprising that dehydrogenation with 2,3,-dichloro-5,6-dicyanobenzoquinone can be effected under basic conditions since the preferred catalyst, as well as the other quinones are sensitive to base, and it is even more surprising that, using less quinone than is required by conventional chemical dehydrogenations, increased yields are obtained.

It has been found that the present process is particularly advantageous for preparing 17-hydroxy-3-oxo-17-α-pregna-4,6-diene-21 carboxylic acid γlactone(17-α- (2-carboxyethyl-17β-hydroxyandrosta-4,6-diene-3-one lactone, canrenone), U.S. Pat. No. 2,900,383, from the corresponding $\Delta^{3,5}$enol ether, 3-ethoxy-17-hydroxy-17-α-pregna-3,5-diene-21 carboxylic acid β-lactone. Accordingly, the present invention is illustrated, in the preferred embodiment, by the preparation of 17-hydroxy-3-oxo-17-α-pregna-4,6-diene-21-carboxylic acid γ-lactone and compared to standard 2,3-dichloro-5,6-dicyanobenzoquinone dehydrogenation of the corresponding $\Delta^{3,5}$enol ether.

EXAMPLE 1

Preparation of 17-hydroxy-3-oxo-17-α-pregna-4,6-diene-21-carboxylic acid γ-lactone by the electrochemical dehydrogenation of 3-ethoxy-17-hydroxy-17-α-pregna-3,5-diene-21-carboxylic acid-γ-lactone using 2,3-dichloro-5,6-dicyanobenzoquinone as the catalyst

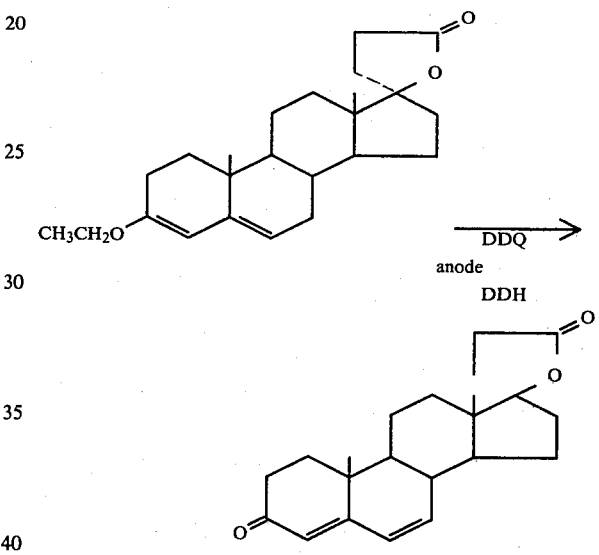

3-Ethoxy-17-hydroxy-17-α-pregna-3,5-diene-21-carboxylic acid-γ-lactone (3.0 g, $8.1\times10^{-3}$ mole), sodium bicarbonate (10.0 g, $1.2\times10^{-2}$ mole) and 2,3-dichloro-5,6-dicyanobenzoquinone (0.3 g, $1.2\times10^{-3}$ mole) were place in the anode compartment of a H cell along with a carbon rod bundle and a silver/silver nitrate reference electrode. The electolyte solution comprising acetonitrile (450 ml, 10.9 mole), water (50 ml, 2.8 mole) and tetraethylammoniumfluoroborate (11.0 g, $5.0\times10^{-2}$ mole), was placed in the anode and cathode chamber along with a 6 cm×2 cm platinum foil cathode. The potentiostat (P.A.R. model 173) was set to deliver +0.7 V vs $Ag/AgNO_3$ with pulsing to −0.500 V for 1 second in every 20 seconds. The potentiostat was engaged and the initial current was 180 MA. The current decayed smoothly to 43 MA over a 5 hour period. Thin layer chromatography indicated the absence of the starting material and the presence of the desired product. Sodium sulfite (5.0 g) was added and the mixture allowed to stir for 1 hour. The acetonitrile was removed on a rotary evaporator and the aqueous residue was extracted twice with 200 ml of ethyl acetate. The ethyl acetate extracts were dried over sodium sulfate, treated with activated carbon and evaporated to dryness to yield 2.8 g of the desired product as yellow crystals. The product was obtained in approximately 93% purity and 93% yield. U.V. λmax=283, absorbance (1 mg%)=0.730, theoretical, 0.785. The product was identical to that obtained in U.S. Pat. No. 2,900,383.

EXAMPLE 2

Preparation of 17-hydroxy-3-oxo-17-α-pregna-4,6-diene-21-carboxylic acid γ-lactone by electrochemical dehydrogenation with 2,3-dichloro-5,6,-dicyanobenzoquinone (DDQ)

The electrochemical reaction of Example 1 was repeated exactly. The initial current was 160 MA and the current decayed to 30 MA over a 3.5 hour period. Thin layer chromatography indicated the absence of the starting enol ether and the presence of the desired product of 94.5% purity in 101.2% yield.

EXAMPLE 3

Preparation of 17-hydroxy-3-oxo-17-α-pregna-4,6-diene-21-carboxylic acid γ-lactone using 1 mole of DDQ by an analogous chemical conversion To 3-ethoxy-17-hydroxy-17-α-pregna-3,5-diene-21-carboxylic acid γ-lactone (3.0 g, $8.1 \times 10^{-3}$ mole) in 440 ml of 10% aqueous electrolyte solution prepared with acetonitrile (450 ml), water (50 ml), tetraethylammoniumfluoroborate (11.0 g, $5.0 \times 10^{-2}$ mole) and sodium bicarbonate (10.0 g, $1.2 \times 10^{-1}$ mole), was added 2,3-dichloro-5,6-dicyanobenzoquinone (1.84 g, $8.1 \times 10^{-3}$ mole) in 60 ml of the above electrolyte solution. The addition was done over a 7 minute period and the reaction temperature went from 19° to 18.5° C. No external cooling was used. The reaction was allowed to stir for 5 hours and thin layer chromatography was conducted at one hour intervals. The reaction did not proceed after the first hour. After 5 hours, 1.02 g of sodium sulfite in 25 ml of water was added and the reaction allowed to stir for one additional hour. The acetonitrile was removed on a rotary evaporator, and the residue diluted with 150 ml of additional water. The aqueous solution was extracted twice with 150 ml of water, saturated potassium bicarbonate and saturated sodium chloride. The resulting crude product was dried over sodium sulfate, filtered, treated with activated charcoal and stripped to yield 2.4 g of product as a glass in 86% crude yield and 53.4% yield of the desired product. U.V. λmax=283, absorbance (1 mg %)=0.49, theoretical=0.785. Purity of product=0.49.0/0.785=62.4%.

EXAMPLE 4

By modifying the above procedure so that solid 2,3-dichloro-5,6-dicyanobenzoquinone in 170 mg portions was added at thirty minute intervals during the first 2 hours of a 5 hour reaction time, 450 ml of acetonitrile and 50 ml of water being initially present in the reaction mixture, 2.7 g of 88% pure product (85% conversion) was obtained.

EXAMPLE 5

By modifying the procedure of Example 3 so that a 5% aqueous acetonitrile solution was used in place of the 10% acetonitrile solution of Example 3, the desired product was obtained in 70.7% purity and 68.2% yield as the pure product. (96.4% crude yield. U.V. λmax=283, absorbance (1 mg%)—0.555, theoretical 0.785.)

EXAMPLE 6

By modifying the procedure of Example 1 so that about 80 mg of 2,3-dichloro-4,6-dicyanobenzoquinone (2.5 weight percent of the starting steroid substrate) was used in place of ten weight percent of Example 1. The yield and product purity was substantially identical with that obtained by the method of Example 1.

EXAMPLE 7

Preparation of 17-α-acetoxy-3-ethoxy-11-β-methyl-19-norpreg-3,5-diene-20-one

17-α-Acetoxy-11-β-methyl-19-norpreg-4-ene-3,20-dione (5.0 g, 0.0134 mole, U.S. Pat. No. 3,527,778) was suspended in dioxane (50 ml), 2B ethanol (0.5 ml), and triethylorthoformate (7.5 ml, 0.041 mole). p-Toluenesulfonic acid monohydrate (0.25 g, 0.0013 mole) was dissolved in dioxane (5 ml) and added to the stirred suspension under a nitrogen atmosphere. The dione slowly went into solution (about 1 hour), forming a yellow solution. The reaction mixture was stirred for two hours thereafter and pyridine (5 ml) added. The solvents were evaporated on a rotary evaporator at 40° C. and a water aspirator. The residue was dissolved in chloroform, washed three times with water, once with saturated sodium chloride solution, dried over sodium sulfate, filtered and stripped to yield 6.7 g of desired product.

EXAMPLE 8

Electrochemical conversion of 17-α-acetoxy-3-ethoxy-11-β-methyl-19-norpreg-3,5-diene-20-one to 17-α-acetoxy-11-β-methyl-19-norpreg-4,6-diene-3,20-dione 17-α-acetoxy-3-ethoxy-11-β-methyl-19-norpregn-3,5-diene-20-one was electrochemically dehydrogenated to 17-α-acetoxy-11-β-methyl-19-norpreg-4,6-diene-3,20-dione following the method of Example 1, using 6.7 g (0.0134 mole) of 3,5-diene, 500 ml of 10% aqueous acetonitrile (made 0.5 N, in tetraethylammoniumfluoroborate), 0.45 g (0.0018 mole) of 2,3-dichloro-5,6-dicyanobenzoquinone, and 5 g of sodium bicarbonate, using a carbon rod bundle anode with a silver/silver nitrate reference electrode and a stainless steel cathode in an H cell. The potentiostat (P.A.R. model 173) was set to deliver +0.5 V vs. Ag/AgNO$_3$ with pulsing to −0.100 V for 3 seconds every 30 seconds.

At the conclusion of the reaction, about 1 g of sodium bisulfite was added and the mixture was refrigerated over night, diluted with water and extracted with ethyl acetate. The ethyl acetate extract was washed twice with water, twice with 5% potassium carbonate, once with 10% sodium bisulfite, twice with water, once with 5% sodium bisulfite, twice with water, once with 5% hydrochloric acid, twice with water, and once with saturated sodium chloride, dried over sodium sulfate and stripped to yield 5.8 g of product.

3.0 g of material was chromatographed on a column packed with neutral alumina and eluted with an ethyl acetate-cyclohexane step gradient. The center cut was taken to provide an ultra-pure sample for labelling purposes in approximately 40% yield, identical with that obtained in U.S. Pat. No. 3,382,986.

I claim:

1. An electrochemical process for dehydrogenating steroidal $\Delta^{3,5}$ enol ethers to provide the corresponding $\Delta^{4,6}$ dienone comprising the steps of reacting a steroidal $\Delta^{3,5}$ enol ether in the present of a high potential catalyst, under basic conditions, with a suitable electolyte solution, at an applied voltage sufficient so that current passes, phenol is oxidized, the $\Delta^{3,5}$ enol remains inert to the anode and the reaction proceeds to completion, and thereafter recovering the steroidal $\Delta^{4,6}$ dienone from the reaction mixture.

2. The process of claim 1 wherein said high potential catalyst is selected from the group consisting of 2,3-dichloro-5,6-dicyanobenzoquinone; 2,3-dichloro-5,6-dicyanohydroquinone, or mixtures thereof, 3,3',5,5'-tetrachloro-4,4'-diphenoquinone, tetrachloro-1,2-benzoquinone, and chloranil.

3. The process of claim 1 or 2 wherein said catalyst is employed in amount of from 2.5 to 10 percent by weight of said $\Delta^{3,5}$ enol.

4. The process of claim 1 or 2 wherein the electrolyte solution comprises an electrolyte selected from the group consisting of an inert soluble salt which is stable to oxidation, and a partially aqueous polar organic solvent system.

5. The process of claim 4 wherein the inert soluble salt is selected from the group consisting of the borate, chloride, perchlorate, sulfonate, phosphate and fluoroborate salts of lithium or tetraloweralkylammonium.

6. The process of claim 5 wherein the partially aqeuous polar organic solvent system comprises a 10–50% aqueous solution of a solvent selected from the group consisting of acetonitrile, dimethylformamide, dioxane and nitromethane.

7. the process of claim 1 wherein the reaction is carried out in a divided H cell.

8. The process of claim 7 wherein the anode is selected from the group consisting of carbon, platnimum, lead oxide, tin oxide and titanium oxide and the cathode is selected from the group consisting of platinum, rhuthenium, nickel, and stainless steel.

9. The process of claim 1 wherein the base is an insoluble or partially soluble base which does not affect lactone chemistry.

10. The process of claim 9 wherein the base is selected from the group consisting of an alkali metal or alkaline earth metal salt.

11. The process of claim 1 or 3 wherein said catalyst is 2,3-dichloro-5,6-dicyanobenzoquinone.

12. The process of claim 1 or 3 wherein said catalyst is selected from the group consisting of 2,3-dichloro-5,6-benzoquinone, 2,3-dichloro--5,6-hydroquinone or mixtures thereof.

13. The process of claim 1 wherein the enol ether is a 19-nor-$\Delta^{3,5}$ enol ether.

14. An electrochemical process for dehydrogenating steroidal $\Delta^{3,5}$ enol ethers to provide the corresponding $\Delta^{4,6}$ dienone comprising the steps of reacting a steroidal $\Delta 3,5$ enol ether in the presence of from about 2.5 to about 10 percent by weight of the enol ether of 2,3-dichloro-5,6-dicyanobenzoquinone under basic conditions with a suitable, partially aqueous electrolyte solution, for a period of from about 2 to about 5 hours at an applied voltage sufficient so that current passes, phenol is oxidized, the enol ether remains inert to the anode and the reaction proceeds to completion, and thereafter recovering the steroidal $\Delta^{4,6}$ dienone from the reaction mixture.

15. The process of claim 14 wherein said electrolyte solution comprises from 10 to 300 percent by weight of the enol ether of an inert soluble salt which is stable to oxidation, and a 10–50 percent aqueous polar organic solvent system.

16. The process of claim 15 wherein said inert soluble salt is selected from the group consisting of the borates, chlorides, perchlorates, sulfonates, phosphates and fluoroborates of lithium or a tetraloweralkylammonium and the organic solvent is selected from the group consisting of acetonitrile, dimethylformamide, dioxane and nitromethane.

17. A method of preparing 17-hydroxy-3-oxo-17-α-pregna-4,6-diene-21-carboxylic acid$\gamma$-lactone from 3-alkoxy-17-hydroxy-17-α-pregna-3,5-diene-21-carboxylic acid$\gamma$-lactone by electrochemical dehydrogenation comprising the steps of reacting said 3-alkoxy-17-hydroxy-17-α-pregna-3,5-diene-21-carboxylic acid$\gamma$-lactone with from 2.5 to 10 weight percent high potential catalyst under basic conditions, at an applied cell potential sufficient that current passes, phenol is oxidized and also the 3,5-diene remains inert to the anode in the absence of phenol.

18. The method of claim 17 wherein said applied cell potential is +0 to 1.5 V vs. Ag/AgNO$_3$.

19. The method of claim 17 wherein said applied cell potential is +0.7 V us Ag/AgNO$_3$.

20. The method of claim 18 or 19 wherein said anode is pulsed to a cathodic potential or no more than −0.5 v for 3 seconds of every 30 seconds.

21. The method of claim 17, 18, 19 or 20 wherein said catalyst is selected from the group consisting of 2,3-dichloro-5,6-dicyanobenzoquinone, 2,3-dichloro-5,6-dicyanohydroquinone of a mixture thereof.

22. The method of claim 17, 18, 19, or 20 wherein said catalyst is 2,3-dichloro-5,6-dicyanobenzoquinone.

23. The method of claim 21 wherein said catalyst is 2,3-dichloro-5,6-dicyanobenzoquinone.

* * * * *